US011596292B2

(12) United States Patent
Reinstein et al.

(10) Patent No.: US 11,596,292 B2
(45) Date of Patent: Mar. 7, 2023

(54) ENDOSCOPE GUIDANCE FROM INTERACTIVE PLANAR SLICES OF A VOLUME IMAGE

(71) Applicant: KONINKLIJKE PHILIPS N.V., Eindhoven (NL)

(72) Inventors: Aryeh Leib Reinstein, Bronx, NY (US); Aleksandra Popovic, Boston, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 657 days.

(21) Appl. No.: 15/745,761

(22) PCT Filed: Jul. 7, 2016

(86) PCT No.: PCT/IB2016/054066
§ 371 (c)(1),
(2) Date: Jan. 18, 2018

(87) PCT Pub. No.: WO2017/013521
PCT Pub. Date: Jan. 26, 2017

(65) Prior Publication Data
US 2018/0214214 A1 Aug. 2, 2018

Related U.S. Application Data

(60) Provisional application No. 62/195,810, filed on Jul. 23, 2015.

(51) Int. Cl.
A61B 1/00 (2006.01)
A61B 5/06 (2006.01)
(Continued)

(52) U.S. Cl.
CPC .......... A61B 1/0004 (2022.02); A61B 1/0016 (2013.01); A61B 1/000094 (2022.02);
(Continued)

(58) Field of Classification Search
None
See application file for complete search history.

(56) References Cited

U.S. PATENT DOCUMENTS 5,970,499 A * 10/1999 Smith ................. G06F 16/40
6,348,058 B1 * 2/2002 Melkent ............ A61B 17/1757
600/429

(Continued)

FOREIGN PATENT DOCUMENTS

WO 2014181222 A1 11/2014

OTHER PUBLICATIONS

Reiter, G. et al., "Mr imaging-based port placement planning for totally endoscopic coronary artery bypass grafting" Interactive Cardovascular and Thoracic Surgery, 3 (2004), pp. 341-345.

Primary Examiner — Michael J Carey
Assistant Examiner — Minqiao Huang

(57) ABSTRACT

An endoscopic imaging system (10) employing an endoscope (20) and an endoscope guidance controller (30). In operation, endoscope (20) generates an endoscopic video (23) of an anatomical structure within an anatomical region. Endoscopic guidance controller (30), responsive to a registration between the endoscopic video (23) and a volume image (44) of the anatomical region, controls a user interaction (50) with a graphical user interface (31) including one or more interactive planar slices (32) of the volume image (44), and responsive to the user interaction (50) with the graphical user interface (31), endoscopic guidance controller (30) controls a positioning of the endoscope (20) relative to the anatomical structure derived from the interactive planar slices (32) of the volume image (44). A robotic endoscopic imaging system (11) incorporates a robot (23) in the endoscopic imaging system (10) whereby endoscope guidance (Continued)

controller (30) controls a positioning by robot (23) of the endoscope (20) relative to the anatomical structure.

11 Claims, 6 Drawing Sheets

(51) Int. Cl.

| | |
|---|---|
| *A61B 34/00* | (2016.01) |
| *A61B 90/00* | (2016.01) |
| *A61B 34/30* | (2016.01) |
| *G16H 30/20* | (2018.01) |
| *A61B 34/20* | (2016.01) |
| *A61B 34/32* | (2016.01) |
| *G06T 7/37* | (2017.01) |
| *G16H 30/40* | (2018.01) |
| *G06T 15/30* | (2011.01) |
| *G16Z 99/00* | (2019.01) |

(52) U.S. Cl.
CPC .............. *A61B 5/066* (2013.01); *A61B 34/20* (2016.02); *A61B 34/25* (2016.02); *A61B 34/30* (2016.02); *A61B 34/32* (2016.02); *A61B 90/36* (2016.02); *A61B 90/37* (2016.02); *G06T 7/37* (2017.01); *G06T 15/30* (2013.01); *G16H 30/20* (2018.01); *G16H 30/40* (2018.01); *A61B 2034/2057* (2016.02); *A61B 2034/2065* (2016.02); *A61B 2034/301* (2016.02); *A61B 2090/365* (2016.02); *G06T 2207/10068* (2013.01); *G06T 2207/10081* (2013.01); *G06T 2207/10088* (2013.01); *G06T 2207/10116* (2013.01); *G16Z 99/00* (2019.02)

(56) References Cited

U.S. PATENT DOCUMENTS

| | | | | |
|---|---|---|---|---|
| 2005/0048456 A1* | 3/2005 | Chefd'hotel | ............ | G06T 7/33 434/267 |
| 2005/0196028 A1* | 9/2005 | Kleen | ............ | G06T 7/33 382/128 |
| 2005/0261550 A1* | 11/2005 | Akimoto | ............ | A61B 1/00009 600/117 |
| 2006/0247517 A1* | 11/2006 | Labadie | ............ | A61B 90/36 600/426 |
| 2007/0019846 A1* | 1/2007 | Bullitt | ............ | G06T 7/0014 382/128 |
| 2007/0127793 A1* | 6/2007 | Beckett | ............ | G06T 7/0012 382/128 |
| 2008/0243142 A1 | 10/2008 | Gildenberg | | |
| 2008/0292164 A1* | 11/2008 | Azar | ............ | G06T 5/50 382/131 |
| 2008/0317204 A1* | 12/2008 | Sumanaweera | ............ | A61B 6/5294 378/65 |
| 2009/0062646 A1* | 3/2009 | Creighton, IV | ............ | A61B 5/062 600/437 |
| 2009/0080779 A1* | 3/2009 | Chefd'hotel | ............ | G06K 9/6206 382/209 |
| 2009/0171184 A1* | 7/2009 | Jenkins | ............ | A61B 90/37 600/411 |
| 2010/0128946 A1* | 5/2010 | Fidrich | ............ | G06T 7/11 382/131 |
| 2011/0282151 A1* | 11/2011 | Trovato | ............ | G06T 7/248 600/117 |
| 2012/0093385 A1* | 4/2012 | Yokosawa | ............ | A61B 5/055 382/131 |
| 2012/0155731 A1* | 6/2012 | Weersink | ............ | G06T 7/344 382/131 |
| 2012/0314919 A1* | 12/2012 | Sparks | ............ | G06K 9/6215 382/128 |
| 2013/0038707 A1 | 2/2013 | Cunningham et al. | | |
| 2013/0315452 A1* | 11/2013 | Berry | ............ | G06T 19/00 382/128 |
| 2014/0022283 A1* | 1/2014 | Chan | ............ | H04N 9/3185 345/633 |
| 2014/0121676 A1* | 5/2014 | Kostrzewski | ............ | A61B 34/30 606/130 |
| 2014/0222157 A1* | 8/2014 | Al Hares | ............ | A61F 2/30942 623/20.34 |
| 2014/0248210 A1* | 9/2014 | Bradbury | ............ | A61P 35/00 424/1.29 |
| 2014/0276001 A1* | 9/2014 | Ungi | ............ | A61B 90/39 600/424 |
| 2014/0301618 A1* | 10/2014 | Popovic | ............ | A61B 90/37 382/128 |
| 2015/0010225 A1* | 1/2015 | Popovic | ............ | A61B 1/00009 382/131 |
| 2015/0126859 A1* | 5/2015 | Popovic | ............ | A61B 90/39 600/426 |

* cited by examiner

ENDOSCOPE GUIDANCE FROM INTERACTIVE PLANAR SLICES OF A VOLUME IMAGE

CROSS-REFERENCE TO PRIOR APPLICATIONS

This application is the U.S. National Phase application under 35 U.S.C. § 371 of International Application Serial No. PCT/IB2016/054066, filed on Jul. 7, 2016, which claims the benefit of U.S. Patent Application No. 62/195,810, filed on Jul. 23, 2015. This application is hereby incorporated by reference herein.

FIELD OF THE INVENTION

The present disclosure generally relates to guidance of an endoscope during a minimally invasive procedure utilizing endoscopic imaging of an anatomical region inclusive of subject anatomical structure(s) (e.g., cardiac surgery, laparoscopic surgery, natural orifice transluminal surgery, single incision laparoscopic surgery, pulmonary/bronchoscopy surgery and diagnostic interventions). The present disclosure specifically relates to an endoscope guidance technique based on a user interaction with interactive planer slices of a volume image of the anatomical region registered to the endoscopic imaging of the anatomical structure(s) within the anatomical region.

BACKGROUND OF THE INVENTION

Minimally invasive surgery is performed using elongated instruments inserted into the patient's body through small ports. The main visualization method during these procedures is endoscopic imaging. In robotic guided minimally invasive surgery, one or more of the instruments is held and controlled by a robotic device, particularly an endoscope.

To aid the minimally invasive surgery team, an image registration is accomplished between the visible endoscopic view and a preoperative three-dimensional ("3D") imaging of the anatomical region (e.g., a CT, a X-ray or a MRI modality). After a registration is completed between preoperative 3D imaging and the live endoscopic video feed, a transform between the preoperative imaging coordinate system and the endoscopic imaging coordinate system is known.

Once the registration is found, as known in the art, an overlay of diagnostically relevant feature(s) of anatomical structure(s) segmented from the preoperative 3D image of the anatomical region are superimposed onto the endoscopic video of the anatomical region to provide a visual aid to the surgical team. Normally, to be able to do this superimposition, a camera calibration matrix must be known, which requires a calibration procedure that is prone to errors and is not practical in a clinical setting. From the calibration, as known in the art, the surgical team guides the robotic system that holds an endoscope toward locations chosen on the overlaid anatomical structures within the endoscopic video, allowing the team to guide the endoscope even if the relevant anatomical feature(s) is(are) hidden in the endoscopic video. Alternative to calibration, as known in the art, movement of the robot may be guided using uncalibrated visual servoing with remote center of motion of the robot.

For the calibrated or uncalibrated endoscope, the robotic system may be guided directly from the preoperative 3D imaging as known in the art. For example, the surgical team selects a point on the preoperative 3D image of the anatomical region, and using the registration between the preoperative imaging coordinate system and the endoscopic imaging coordinate system, the highlighted point is transformed into the associated point on the live endoscope video. The robotic system then guides the endoscope towards that point as known in the art.

There are several issues that may arise with the aforementioned known guidance of an endoscope during a minimally invasive procedure.

First, feature(s) of an anatomical structure segmented from the preoperative 3D image by themselves may be difficult to navigate and orientate in order to select the desired viewing location of the anatomical structure (e.g. an arterial tree segment from a preoperative 3D image of a heart may be difficult to navigate and orientate in order to select the desired viewing location of the heart). Furthermore, if the segmentation of the anatomical feature(s) is insufficient, then the anatomical structure is even more difficult to navigate.

Second, the surgical team may be more accustomed to analyzing and navigating slices of the preoperative 3D image (e.g., axial, coronal and sagittal image slices) as opposed to the 3D volume itself.

Third, typical 3D visualization of a segmented preoperative image only enables the surgical team to see surface features on the segmented anatomical structure, and thus not allowing the surgical team to navigate the robotic system based on internal features of the anatomical structure illustrated within the preoperative 3D image.

SUMMARY OF THE INVENTION

The present disclosure provides inventions for displaying interactive planar slices of a volume image of an anatomical region whereby a surgical team may manipulate the interactive planar slices to find areas of interest, internal or external, to an anatomical structure of interest within the anatomical region (e.g., an organ), and manually or robotically guide the endoscope to point towards that highlighted area of interest. More particularly, the inventions of the present disclosure may facilitate a selection by the user of point(s) of interest of the anatomical structure that are not visible in the live endoscope video feed and/or even in the 3D volume data, and manually or robotically navigate the endoscope towards that interest point within the anatomical region.

One form of the inventions of the present disclosure is an endoscopic imaging system employing an endoscope and an endoscope guidance controller. By structural design, the endoscope is operable to generate an endoscopic video of an anatomical structure within an anatomical region. The endoscope guidance controller, responsive to a registration between the endoscopic video and a volume image of the anatomical region, is operable to control a user interaction with a graphical user interface including one or more interactive planar slices of the volume image. Responsive to the user interaction with the graphical user interface, the endoscope guidance controller is further operable to control a positioning of the endoscope relative to the anatomical structure derived from the interactive planar slice(s) of the volume image.

A second form of the inventions of the present disclosure is a robotic endoscopic imaging system incorporating a robot into the endoscopic imaging system. Specifically, responsive to the user interaction with the graphical user interface, the endoscope guidance controller is operable to control a positioning by the robot of the endoscope relative to the anatomical structure derived from the interactive planar slice(s) of the volume image.

For purposes of the inventions of the present disclosure, the term "endoscope" broadly encompasses any device structurally configured with ability to image from inside a body as understood in the art of the present disclosure and as exemplary described herein. Examples of an endoscope include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, colposcope, thoracoscope, sygmoidscope, neuroendoscope, etc.) and any device similar to a scope that is equipped with an image system). The imaging is local, and surface images may be obtained optically with fiber optics, lenses, and miniaturized (e.g. CCD based) imaging systems (e.g., laparoscopic ultrasound).

For purposes of the inventions of the present disclosure, the term "controller" broadly encompasses all structural configurations of an application specific main board or an application specific integrated circuit housed within or linked to a workstation for controlling an application of various inventive principles of the present disclosure as subsequently described herein. The structural configuration of the controller may include, but is not limited to, processor(s), computer-usable/computer readable storage medium(s), an operating system, application module(s), peripheral device controller(s), slot(s) and port(s).

Examples of the workstation include, but are not limited to, an assembly of one or more computing devices (e.g., a client computer, a desktop and a tablet), a display/monitor, and one or more input devices (e.g., a keyboard, joysticks and mouse). For purposes of the inventions of the present disclosure, the term "application module" broadly encompasses a component of the controller consisting of an electronic circuit and/or an executable program (e.g., executable software and/firmware) for executing a specific application.

For purposes of the inventions of the present disclosure, the label "endoscope guidance" used herein for the term "controller" serves to identify the controller as described and claimed herein without specifying or implying any additional limitation to the term "controller".

For purposes of the inventions of the present disclosure, the term "robot" broadly encompasses any robotic device structurally configured with motorized control of one or more joints for maneuvering an end-effector as desired for a particular endoscopic procedure. Examples of a robot include, but are not limited to, a serial robot having joints serially connected with rigid segments, a parallel robot having joints and rigid segments mounted in parallel order (e.g., a Stewart platform known in the art) or any hybrid combination of serial and parallel kinematics.

For purposes of the inventions of the present disclosure, the term "endoscopic video" broadly encompasses a stream of visual images generated by an endoscope as known in the art, and the term "volume image" broadly encompasses any preoperative or intraoperative 3D image data as known in the art (e.g., CT, MRI or X-ray).

For purposes of the inventions of the present disclosure, terms of the art including, but not limited to, "registration", "display", "graphical user interface", "user interaction", "user navigation", "user selection" and "point of interest" are to be interpreted as understood in the art of the present disclosure and as exemplary described herein.

For purposes of the inventions of the present disclosure, the term "interactive planar slice" broadly encompasses a planar image of a volume image that is an interactive component of the graphical user interface.

For purposes of the inventions of the present disclosure, the terms "responsive" and "derived", and any word tenses thereof are to be interpreted as understood in the art of the present disclosure and as exemplary described herein.

A third form of the inventions of the present disclosure is a robotic endoscopic imaging method involving the endoscope generating the endoscopic video of the anatomical structure within the anatomical region. The robotic endoscopic imaging method further involves the endoscope guidance controller, responsive to the registration between the endoscopic video and the volume image of the anatomical region, controlling a user interaction with a graphical user interface including the interactive planar slice(s) of the volume image, and the endoscope guidance controller, responsive to the user interaction with the graphical user interface, controlling the positioning by the robot of the endoscope relative to the anatomical structure derived from the interactive planar slice(s) of the volume image.

The foregoing forms and other forms of the present disclosure as well as various features and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

DETAILED DESCRIPTION OF THE PREFERRED EMBODIMENTS

Figure 1:
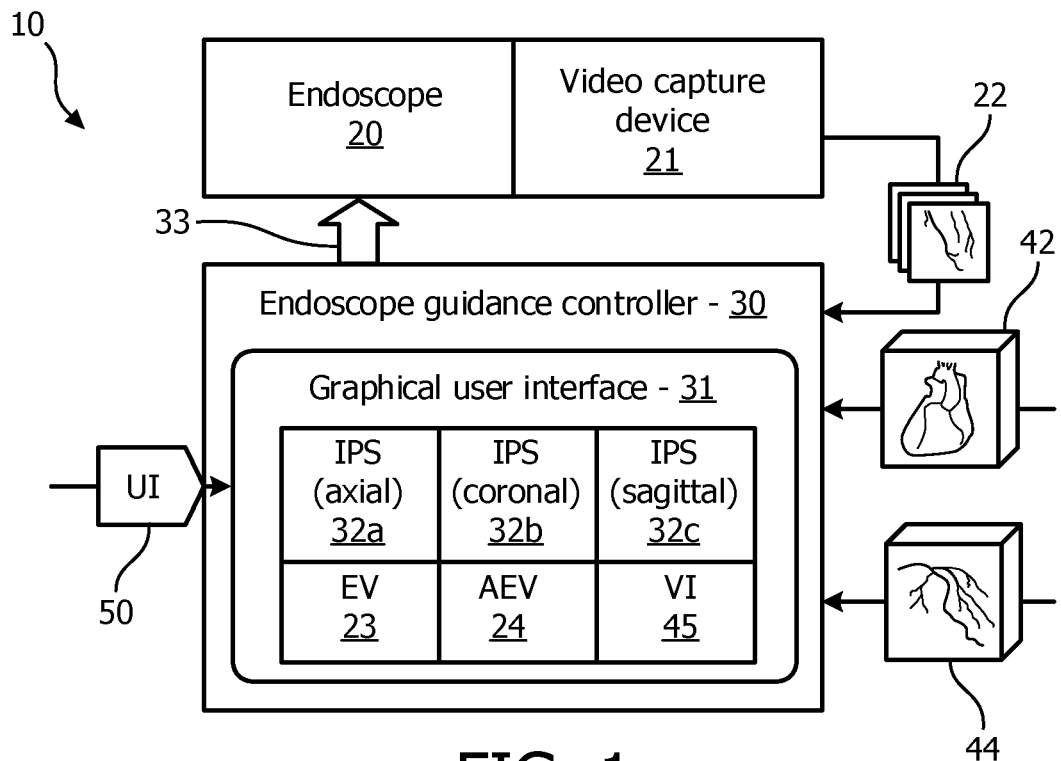
FIG. 1 illustrates an exemplary embodiment of an endoscopic imaging system in accordance with the inventive principles of the present disclosure.
Figure 2:
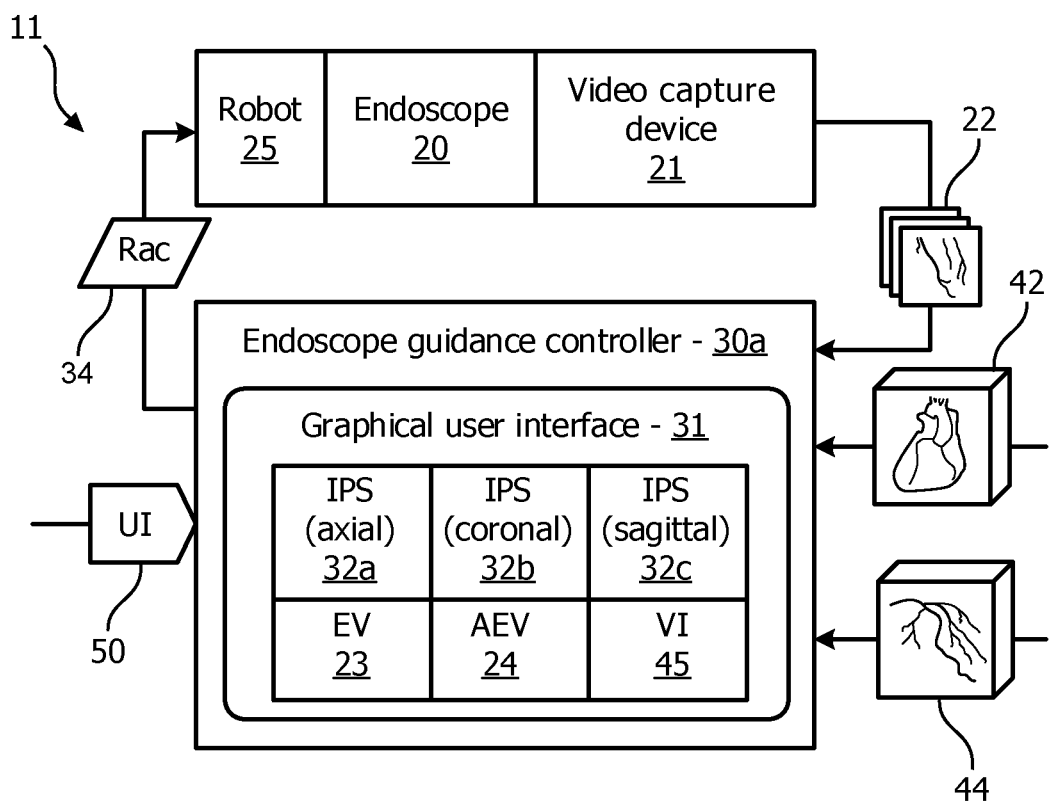
FIG. 2 illustrates an exemplary embodiment of a robotic endoscopic imaging system in accordance with the inventive principles of the present disclosure.

To facilitate an understanding of the present disclosure, the following description of FIGS. 1 and 2 teaches basic inventive principles of an endoscopic imaging system 10 and a robotic endoscopic imaging system 11, respectively, during an exemplary cardiac surgery. From the description of FIGS. 1 and 2, those having ordinary skill in the art will appreciate how to apply the inventive principles of the present disclosure for any type of minimally invasive procedure utilizing an endoscope, particularly an endoscope held by an articulated platform or a robot.

Referring to FIG. 1, endoscopic imaging system 10 employs an endoscope 20, a video capture device 21 and endoscope guidance controller 30.

For the cardiac surgery, endoscope 20 is inserted into a patient's body through a small port into a cardiac region of the patient as known in the art. In operation, endoscope 20 is strategically positioned within the port to generate an endoscopic image of a heart within the cardiac region of the patient, and video capture device 21 converts the endoscopic image from endoscope 20 into an endoscopic video of computer readable temporal sequence of digital frames 22.

Endoscope guidance controller 30 processes both the digital frames of the endoscopic video 23 and a volume image 42 of heart segmented from the cardiac region (e.g., a preoperative or intraoperative CT, MRI or X-ray 3D image of the segmented heart), and executes a registration routine for registering endoscopic video 23 and volume image 42 whereby a transformation between an imaging coordinate system of endoscope 20 and an imaging coordinate system of the volume imaging modality is known.

In practice, any type of registration routine may be executed by endoscope guidance controller 30. In one embodiment for coronary artery bypass grafting as known in the art, endoscope guidance controller 30 executes a registration routine involving a matching of an arterial tree extracted from the segmented heart of volume image 42 to branches of the arterial tree viewed within endoscopic video 23. For this embodiment, endoscope guidance controller 30 may extract the arterial tree from the segmented heart of volume image 42 as known in the art, or process a volume image 44 of an extracted arterial tree.

Based on the image registration, a user selection of a point of interest on volume image 42 may be used to transform that point of interest into an associated point within the imaging coordinate system of endoscope 20 whereby endoscope 20 may be guided towards the associated point for imaging such point within the endoscopic video. To this end, endoscope guidance controller 30 controls a user interaction ("UI") 50 with a graphical user interface 31 including one or more interactive planar slice(s) 32 of volume image 44. Examples of an interactive planar slice 32 include, but are not limited to, an interactive axial slice 32a, an interactive coronal slice 32b and an interactive sagittal slice 32c as shown.

To facilitate user interaction 50, in practice, graphical user interface 31 displays graphical icons, visual indicators, etc. for interfacing with interactive planar slice(s) 32. In one embodiment, graphical user interface 31 displays a slice selector of segmented volume image 42 and/or a screen slider for each displayed planer view of segmented volume image 42 whereby a hardware input device (e.g., a mouse, a keyboard, a joystick, a touchpad, etc.) may be user operated to manipulate the slice selector and/or screen slider as known in the art.

User interaction 50 involves a user navigation through interactive planar slice(s) 32 of volume image 42 whereby the user may select particular planar view(s) of the segmented heart within volume image 42 to guide endoscope 20 within the cardiac region for positioning endoscope 20 with a field-of-view of endoscope 20 corresponding to the selected planar view(s) of the segmented heart. Alternatively, from the user selection of particular planar view(s) on interest of the segmented heart, the user may further select particular point(s) of interest within the selected planar view(s) for positioning endoscope 20 with a field-of-view of endoscope 20 corresponding to the selected point(s) of interest of the segmented heart.

To supplement user interaction 50, in practice as known in the art, graphical user interface 31 may further include a display of an endoscopic video 23 of digital frames 22, an expanded endoscopic video 24 of volume image 42, and a volume image 45 of a rotatable segmented heart. In one embodiment, an overlay of the extracted arterial tree of volume image 44 may be overlaid on endoscopic video 23 and/or endoscopic video 24 as known in the art, and volume image 42 may be shown with a different coloring of the segmented heart and extracted arterial tree as known in the art.

For guidance purposes of endoscope 20, in practice as known in the art, endoscope guidance controller 30 ascertains any spatial differential and/or any angular differential between a current planar view of endoscopic video 23, and a user selection of a planar view of interest and/or a point of interest via interactive planar slice(s) 32 of volume image 42. From an ascertained spatial differential and/or an ascertained angular differential, endoscope guidance controller determines an endoscopic path to position endoscope 20 for imaging the user selected planar view and/or the user selected point of interest. For the determination of the endoscopic path, endoscope guidance controller 30 finds a center location of the user selected planar view and/or a location of the user selected point of interest from a camera calibration matrix of endoscope 20 as known in the art, or from an uncalibrated visual servoing of endoscope 20 as known in the art involving an overlay of extracted arterial tree of volume image 44 upon endoscopic video 23 and/or segmented heart of volume image 42.

For a manual guidance of endoscope 20, the determined endoscopic path is visually and/or audibly communicated 33 to the user of system 10 whereby the user may, by hand and/or a manipulation of an articulated platform/robot, linearly displace, pivot and/or revolve endoscope 20 relative to the incision port of the patient by a specified distance and/or specified degrees to position endoscope 20 for imaging the user selected planar view and/or the user selected point of interest.

Referring to FIG. 2, for an automatic robotic guidance of endoscope 20, system 11 incorporates a robot 25 with system 10 for controlling endoscope 20 and an embodiment 30a of endoscope guidance controller 30 communicates robot actuation commands 34 as known in the art to robot 25 for linearly displacing, pivoting and/or revolving endoscope 20 relative to the incision port of the patient by a specified distance and/or specified degrees to position endoscope 20 for imaging the user selected planar view and/or the user selected point of interest.

To facilitate a further understanding of the inventive principles of the present disclosure, the following description of FIGS. 3-9 further teaches inventive principles of the present disclosure for an embodiment of robotic endoscopic imaging system 11 employing a spherical robot 25a holding an oblique endoscope 23a, and a workstation 12 having endoscope guidance controller 30a installed therein. From the description of FIGS. 3-9, those having ordinary skill in the art will further appreciate how to apply the inventive principles of the present disclosure for any type of minimally invasive procedure utilizing an endoscope, particularly an endoscope held by a robot.

Figure 3:
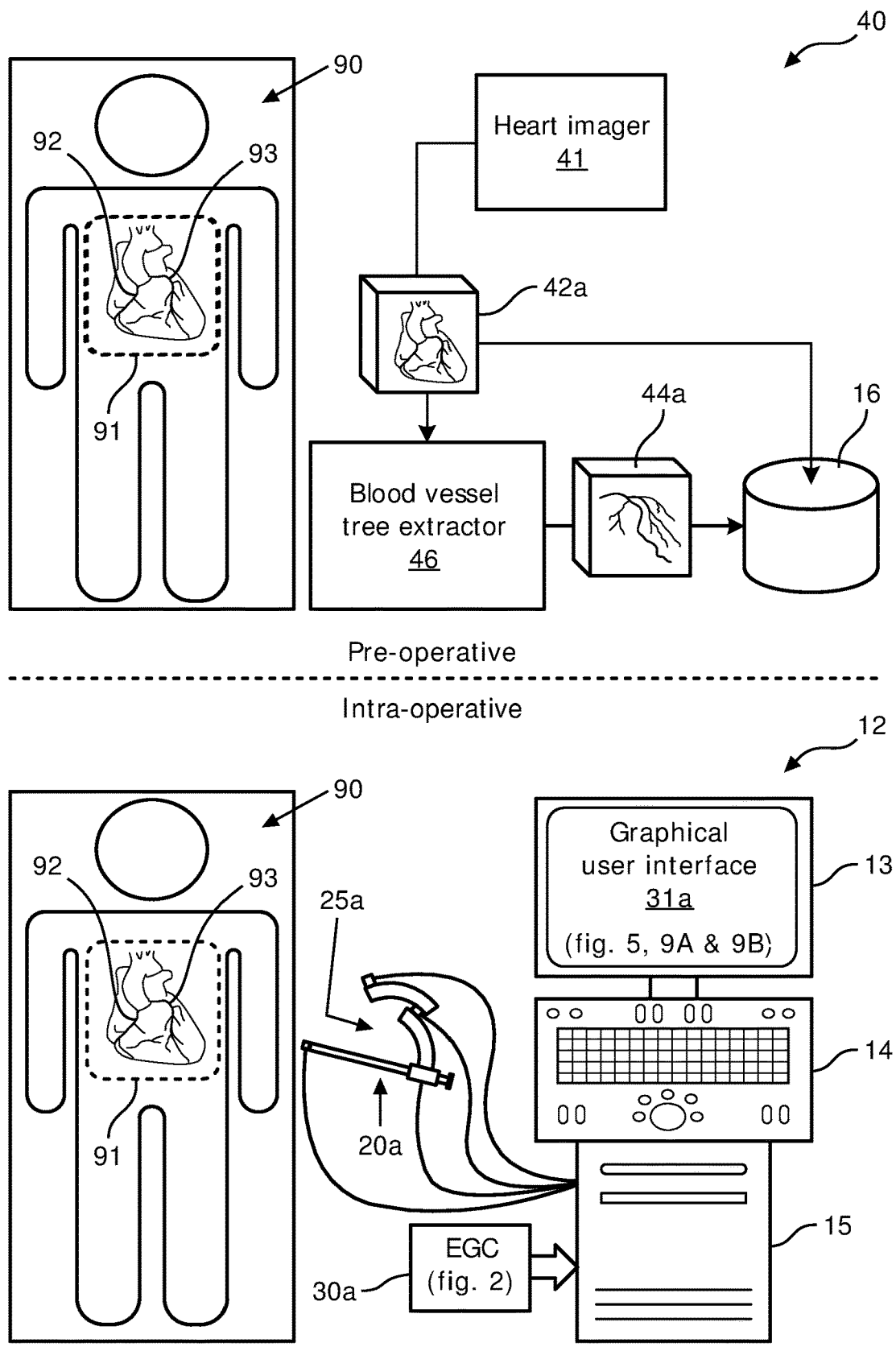
FIG. 3 illustrates a minimally invasive cardiac procedure utilizing an exemplary embodiment of the robotic endoscopic imaging system illustrated in FIG. 2 in accordance with the inventive principles of the present disclosure.

Referring to FIG. 3, an imaging modality 40 (e.g., a CT, MRI or X-ray modality) includes application modules in the form of a heart imager 41 and a blood vessel tree extractor 43 as known in the art, and workstation 12 includes a known arrangement of a monitor 13, a keyboard 14, a computer 15 and a database 16.

Figure 4:
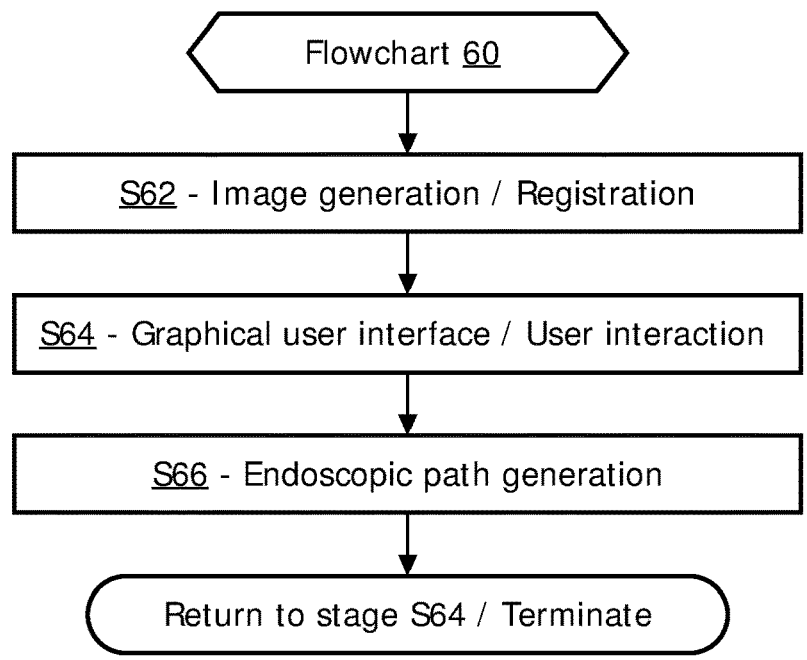
FIG. 4 illustrates a flowchart representative of an exemplary embodiment of an endoscopic imaging method in accordance with the inventive principles of the present disclosure.

Referring to FIGS. 3 and 4, for a preoperative phase, a patient 90 is positioned on an operating table for imaging of a cardiac region 91 of patient 90 by imaging modality 40 during a preoperative stage S62 of flowchart 60. Specifically, stage S62 encompasses heart imager 41 generating segmented volume image 42a of heart 92 and blood vessel tree extractor 46 generating extraction volume image 44a of a blood vessel tree 93 associated with heart 92. Both images 42a and 44a are stored within database 16 of workstation 12.

An intraoperative phase involves oblique endoscope 20a being inserted into patient 90 through a small port into a cardiac region of patient 90 as known in the art. In operation, oblique endoscope 20a is strategically positioned within the port to initiate a generation by oblique endoscope 20a of an endoscopic video of heart 92 of patient 90, and endoscopic guidance controller 30a controls a further positioning by spherical robot 25a of oblique endoscope 20a relative to heart 92 for imaging a user selected planar view and/or a user selected point of interest of heart 92 in accordance with the inventive principle of graphical user interface 31a of the present disclosure.

Specifically, an intraoperative stage S64 of flowchart 60 encompasses a user interaction via keyboard 14 with graphical user interface 31a as displayed on monitor 13 of workstation 12.

Figure 5:
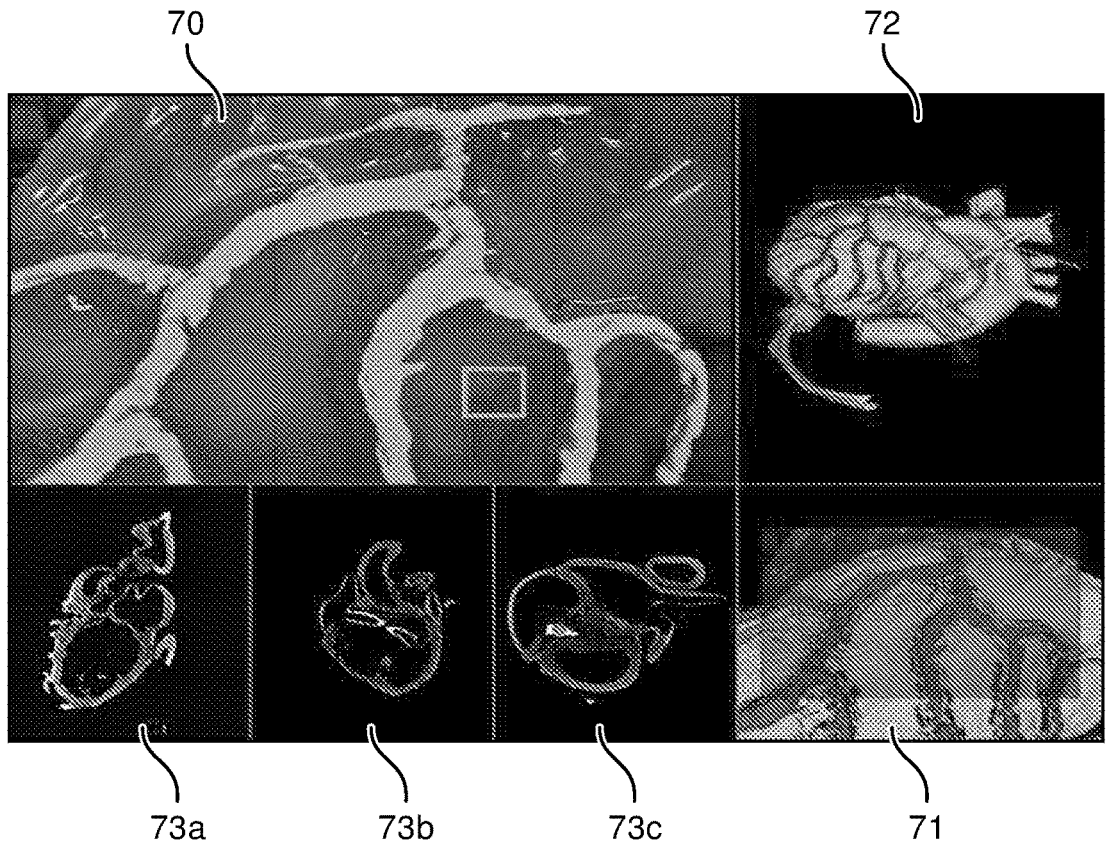
FIG. 5 illustrates an exemplary embodiment of a graphical user interface including a segmented volume image in accordance with the inventive principles of the present disclosure.

In one embodiment as shown in FIG. 5, graphical user interface 31a includes a display of:

(1) an endoscopic video 70 of heart 92 (FIG. 3); having an overlay of the extracted arterial tree of volume image 44a (2) an augmented endoscopic video 71 of volume image 44a;

(3) a volume image 72 of a rotatable segmented heart from volume image 42a; and (4) interactive axial slice 73a, interactive coronal slice 73b and interactive sagittal slice 73c of volume image 42a (FIG. 3).

Figure 8A:
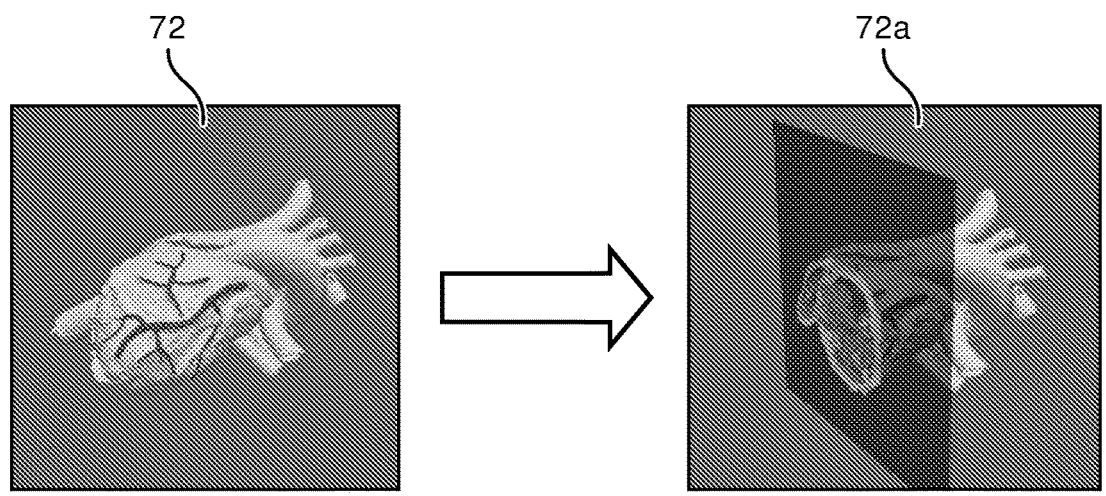
FIGS. 8A and 8B illustrate exemplary embodiments of a clipping of a segmented volume image in accordance with the inventive principles of the present disclosure.
Figure 9A:
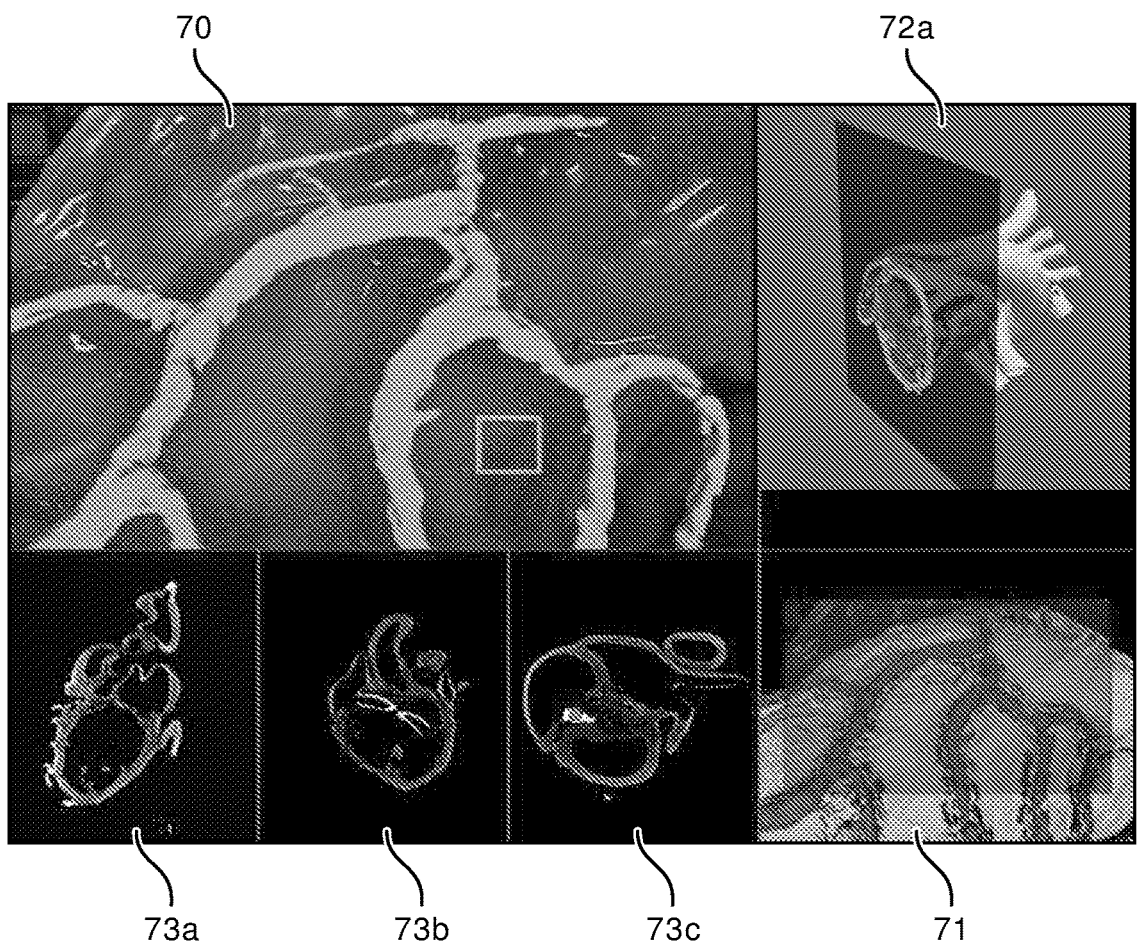
FIGS. 9A and 9B illustrate exemplary embodiments of a graphical user interface including a clipped segmented volume image in accordance with the inventive principles of the present disclosure.

In a second embodiment, volume image 72 may be clipped by a user selection of an interactive planar slice as shown FIG. 8A and a clipped volume image 72a inclusive of the interactive planar slice may be displayed by graphical user interface 31a as shown in FIG. 9A.

Figure 8B:
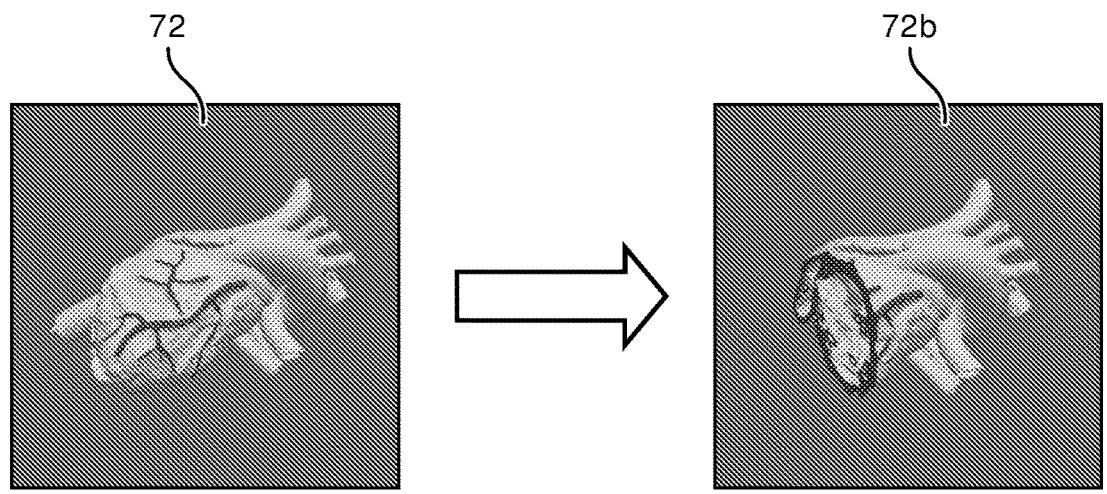
Figure 9B:
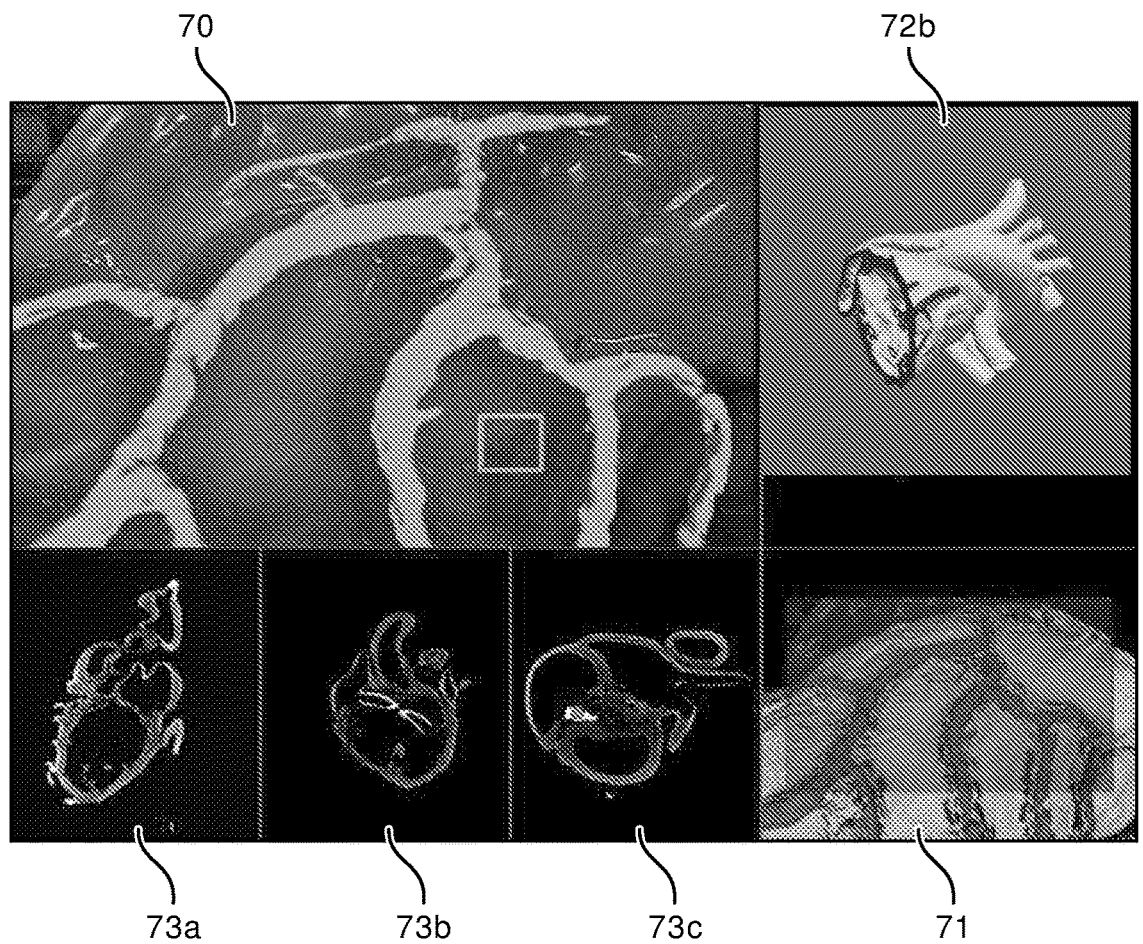

In a third embodiment, volume image 72 may be clipped by a user selection of an interactive planar slice as shown FIG. 8B and a clipped volume image 72b inclusive of the interactive planar slice may be displayed by graphical user interface 31a as shown in FIG. 9B.

The user interaction may involve a user navigation through one of interactive planar slices 73a-73c via volume image 42a via activation of a slice selector as known in the art whereby the user may select a particular planar view of the segmented heart within volume image 42a to guide oblique endoscope 20a within the cardiac region for positioning oblique endoscope 20a via spherical robot 25a with a field-of-view of oblique endoscope 20a corresponding to the selected planar view of the segmented heart.

In practice, endoscope guidance controller 30a may display a user selection of the planar view of volume image 42a for user guidance contemplation purposes without any movement of oblique endoscope 20a by robot 25a until receiving a user confirmation of the user selection of the point of interest. Furthermore for user guidance contemplation purposes, the user selected planar view may displayed within augmented endoscopic video 71 and/or the segmented heart of volume image 42a may be rotated to centralize the user selected planar view.

Figure 6A:
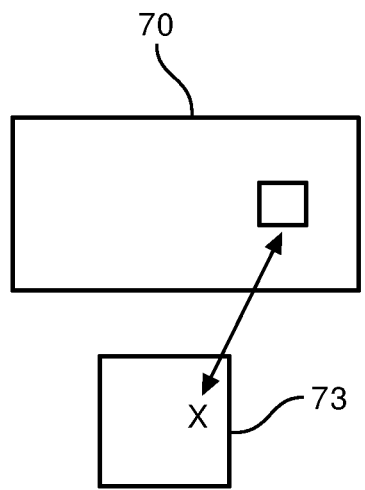
FIG. 6A illustrates an exemplary embodiment of a user selection of a point of interest within an interactive planar slice in accordance with inventive principles of the present invention.

The user interaction may further involve a user navigation through one of interactive planar slices 73a-73c of volume image 42a via the slice selector as known in the art whereby the user may select a particular point of interest within a selected planar view for positioning oblique endoscope 20a via spherical robot 25a with a field-of-view of oblique endoscope 20a corresponding to the selected point of interest of the segmented heart. For example, as shown in FIG. 6A, a user selection of a point of interest symbolized by an X in interactive planar slice 73 is represented by a box in endoscopic video 70 for analytical purposes. Furthermore, a corresponding box may be displayed within augmented endoscopic video 71 and/or the segmented heart of volume image 42a may be rotated to centralize the user selected point of interest.

In practice, endoscope guidance controller 30a may display a user selection of a point of interest on an interactive planar slice of volume image 42a for user guidance contemplation purposes without any movement of oblique endoscope 20a by spherical robot 25a until receiving a user confirmation of the user selection of the point of interest. Furthermore for user guidance contemplation purposes, the users selected point of interest may be displayed within augmented endoscopic video 71 and/or the segmented heart of volume image 42a may be rotated to centralize the user selected point of interest.

Figure 6B:
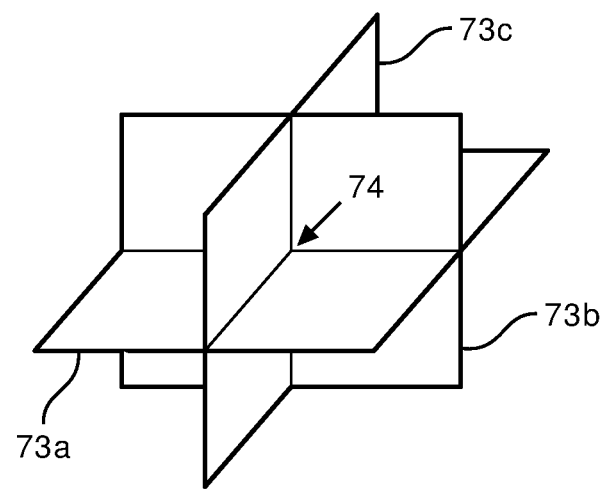
FIG. 6B illustrates an exemplary embodiment of an intersection of orthogonal interactive planar slices in accordance with the inventive principles of the present disclosure.

The user interaction may further involve a user navigation through one or more interactive planar slices 73a-73c of volume image 42a via the slice selector as known in the art whereby the user may select a particular point of interest corresponding to an orthogonal intersection of interactive planar slices 73a-73c for positioning oblique endoscope 20a via spherical robot 25a with a field-of-view of oblique endoscope 20a corresponding to the selected point of interest of the segmented heart. For example, as shown in FIG. 6B, a user navigation through interactive planar slices 73a-73c selects a point of interest 74 corresponding to an orthogonal intersection of interactive planar slices 73a-73c.

In practice, endoscope guidance controller 30a may display an orthogonal intersection of interactive planer images 73a-73c of volume image 42a for user guidance contemplation purposes without any movement of oblique endoscope 20a by robot 25a until receiving a user confirmation of the user selection of the point of interest. Furthermore for user guidance contemplation purposes, the orthogonal intersection of interactive planar slices 73a-73c may be displayed within augmented endoscopic video 71 and/or the segmented heart of volume image 42a may be rotated to centralize the orthogonal interaction of interactive planar slices 73a-73c.

Referring back to FIGS. 3 and 4, an intraoperative stage S66 of flowchart 60 encompasses endoscope guidance controller 30a generating an endoscopic path corresponding to the user selected planar view and/or the user selected point of interest.

Specifically, endoscope guidance controller 30 ascertains any spatial differential and/or any angular differential between a current planar view of endoscopic video 70, and a user selection of a planar view of interest and/or a point of interest via interactive planar slice(s) 73a-73c of volume image 42a. From an ascertained spatial differential and/or an ascertained angular differential, endoscope guidance controller determines an endoscopic path to position oblique endoscope 20a for imaging the user selected planar view and/or the user selected point of interest. For the determination of the endoscopic path, endoscope guidance controller 30 finds a center location of the user selected planar view and/or a location of the user selected point of interest from a camera calibration matrix of endoscope 20 as known in the art, or from an uncalibrated visual servoing of endoscope 20 as known in the art involving an overly of extracted arterial tree of volume image 44a upon endoscopic video 23 and/or segmented heart of volume image 42a.

Figure 7:
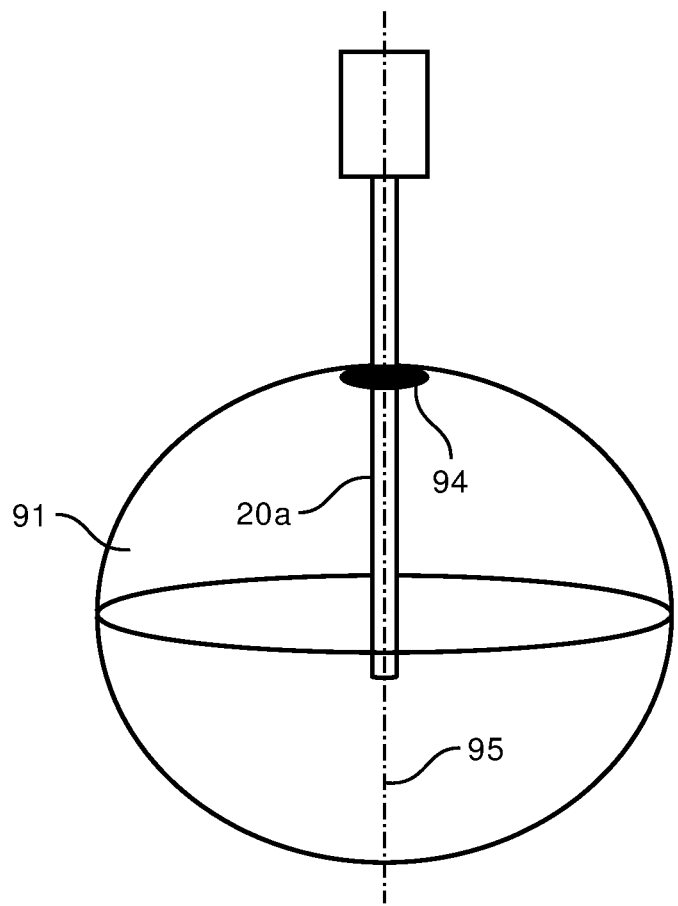
FIG. 7 illustrates an exemplary embodiment of a positioning control of an endoscope in accordance with the inventive principles of the present disclosure.

For automatic robotic guidance of oblique endoscope 20a, endoscope guidance controller 30a communicates robot actuation commands as known in the art to spherical robot 25a for pivoting and/or revolving oblique endoscope 20a relative to the incision port of the patient by specified degrees to position oblique endoscope 20a for imaging the user selected planar view and/or the user selected point of interest. For example, as shown in FIG. 7, a longitudinal axis 95 of an incision point 94 of patient 90 into cardiac region 91 serves as a basis for pivoting and/or revolving oblique endoscope 20a relative to the incision port 94 by specified degrees to position oblique endoscope 20a for imaging the user selected planar view and/or the user selected point of interest.

Referring back to FIGS. 3 and 4, after an initial endoscope path generation during stage S66, endoscope guidance controller 30a may return to stage S64 for additional user interaction with graphical user interface 31a or terminate upon completion of the procedure.

Referring to FIGS. 1-9, those having ordinary skill in the art will appreciate numerous benefits of the present disclosure including, but not limited to, robust techniques for endoscopic guidance, particularly robotic, within an anatomical region.

Furthermore, as one having ordinary skill in the art will appreciate in view of the teachings provided herein, features, elements, components, etc. described in the present disclosure/specification and/or depicted in the FIGS. 1-9 may be implemented in various combinations of electronic components/circuitry, hardware, executable software and executable firmware and provide functions which may be combined in a single element or multiple elements. For example, the functions of the various features, elements, components, etc. shown/illustrated/depicted in the FIGS. 1-9 can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, circuitry, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present disclosure can take the form of a computer program product or application module accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk read only memory (CD-ROM), compact disk read/write (CD-R/W) and DVD. Further, it should be understood that any new computer-readable medium which may hereafter be developed should also be considered as computer-readable medium as may be used or referred to in accordance with exemplary embodiments of the present disclosure and disclosure.

Having described preferred and exemplary embodiments of novel and inventive endoscope guidance from volume image slices, (which embodiments are intended to be illustrative and not limiting), it is noted that modifications and variations can be made by persons having ordinary skill in the art in light of the teachings provided herein, including the FIGS. 1-9. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present disclosure. Further, corresponding and/or related method for manufacturing and/or using a device and/or system in accordance with the present disclosure are also contemplated and considered to be within the scope of the present disclosure.

The invention claimed is:

1. An endoscopic imaging system, comprising:
an endoscope for generating an endoscopic video of an anatomical structure within an anatomical region; and
an endoscope guidance controller operably connected to the endoscope, the endoscopic guidance controller structurally configured to:
based on a registration between the endoscopic video and a volume image of the anatomical region, control a graphical user interface to facilitate a user interaction with a slice selector configured to select and display at least one interactive planar slice of the volume image, the selected at least one interactive planar slice corresponding to a selected planar view of the anatomical structure, the user interaction comprising a user selection of a point of interest within the at least one interactive planar slice, and
based on the selected planar view and the selected point of interest, guide the endoscope to a location within the anatomical region and position the endoscope to adjust a field of view of the endoscope to align with the selected planar view of the anatomical structure for imaging the selected point of interest within the endoscopic video.

2. The endoscopic imaging system of claim 1, wherein the at least one interactive planar slice comprises at least one of:
an interactive axial slice of the volume image;
an interactive coronal slice of the volume image; and
an interactive sagittal slice of the volume image.

3. The endoscopic imaging system of claim 1, wherein:
the endoscopic guidance controller is responsive to a user navigation through a plurality of interactive planar slices of the volume image, and
the endoscopic guidance controller is further responsive to a user selection of the at least one interactive planar slice of the volume image derived from the user navigation through the plurality of interactive planar slices of the volume image.

4. The endoscopic imaging system of claim 1, wherein:
the graphical user interface further comprises a display of the endoscopic video;
the endoscopic guidance controller is responsive to the user selection of a point of interest within the at least one interactive planar slice of the volume image; and
the endoscopic guidance controller controlling a display of the user selection of the point of interest within the endoscopic video.

5. The endoscopic imaging system of claim 1, wherein:
the graphical user interface further comprises a display of a volume segmentation of the anatomical structure derived from the volume image; and
the endoscopic guidance controller is further configured to display a clipping of the volume segmentation of the anatomical structure derived from the at least one interactive planar slice of the volume image.

6. The endoscopic imaging system of claim 5, wherein the endoscopic guidance controller is further responsive to a user selection of a point of interest within the clipping of the volume segmentation of the anatomical structure.

7. The endoscopic imaging system of claim 1, wherein the graphical user interface further comprises:
the endoscopic video of the anatomical structure within the anatomical region; and
an augmented endoscopic view of the volume image of the anatomical region.

8. The endoscopic imaging system according to claim 1, further comprising:
a robot operably connected to the endoscopic guidance controller and the endoscope, the robot configured to position the endoscope relative to the anatomical structure within the anatomical region based on control by the endoscopic guidance controller.

9. The endoscopic imaging system according to claim 1, wherein the endoscope guidance controller is configured to determine a spatial differential between a current planar view of the endoscopic video and the selected planar view; and wherein the endoscope guidance controller is configured to guide the endoscope to adjust the field of view based on the determined spatial differential.

10. The endoscopic imaging system according to claim 1, wherein the endoscope guidance controller is configured to determine an angular differential between a current planar view of the endoscopic video and the selected planar view; and wherein the endoscope guidance controller is configured to guide the endoscope to adjust the field of view based on the determined angular differential.

11. The endoscopic imaging system according to claim 1, wherein the endoscope guidance controller is configured to determine a spatial differential and an angular differential between a current planar view of the endoscopic video and the selected planar view; and wherein the endoscope guidance controller is configured to guide the endoscope to adjust the field of view based on the determined spatial differential and angular differential.

* * * * *